US00PP23540P3

(12) United States Plant Patent
Pesteil

(10) Patent No.: US PP23,540 P3
(45) Date of Patent: Apr. 16, 2013

(54) ***CHRYSANTHEMUM* PLANT NAMED 'PLUM CRAZY'**

(50) Latin Name: ***Chrysanthemum×morifolium* Ramat.**
Varietal Denomination: Plum Crazy

(75) Inventor: Celine Emmanuelle Veronique Pesteil, Chichester (GB)

(73) Assignee: Chrysanthemum Breeders Association Research B.V., Valkenburg Z-H (NL)

( * ) Notice: Subject to any disclaimer, the term of this patent is extended or adjusted under 35 U.S.C. 154(b) by 257 days.

(21) Appl. No.: 13/064,408

(22) Filed: Mar. 23, 2011

(65) Prior Publication Data
US 2012/0246775 P1 Sep. 27, 2012

(51) Int. Cl.
*A01H 5/00* (2006.01)

(52) U.S. Cl. ..... Plt./287

(58) Field of Classification Search ..... Plt./287
See application file for complete search history.

*Primary Examiner* — Kent L Bell
(74) *Attorney, Agent, or Firm* — Steptoe & Johnson LLP

(57) ABSTRACT

A new variety of *Chrysanthemum* plant named 'Plum Crazy', characterized by its good uniform canopy of dark purple flowers. The new variety has a medium vigor, a free branching and uniform spreading habit, a good foliage presentation and inflorescences week 38 in natural season.

1 Drawing Sheet

Latin name of the genus and species: Botanical Classification: *Chrysanthemum×morifolium* Ramat.

Variety denomination: The new *Chrysanthemum* variety denomination is 'Plum Crazy'.

BACKGROUND OF THE INVENTION

The present invention comprises a new and distinct cultivar of *Chrysanthemum* botanically known as *Chrysanthemum×morifolium* Ramat., and referred to by the cultivar name 'Plum Crazy', identified as 30769-0 originated from a cross made in a controlled breeding program in Chichester, West Sussex, United Kingdom. The new and cultivar was discovered and selected as a flowering plant in September 2000.

The female parent of the new variety is an undistributed, unpatented seedling identified as G69D2 and the male parent is the unpatented variety 'Cyblis'.

The new variety 'Plum Crazy' has been asexually reproduced by vegetative cuttings in Chichester, West Sussex, United Kingdom and the distinguishing characteristics are retained through successive generations of asexual reproduction.

BRIEF SUMMARY OF THE INVENTION

'Plum Crazy' is a garden type of *Chrysanthemum* plant variety having a uniformed domed capitulum of dark purple decorative type inflorescences.

Comparison with Female Parent

Plants of the new *Chrysanthemum* variety 'Plum Crazy' are dissimilar to the female parent 'G69D2' in plant habit and growth rate. In side-by-side comparisons in Chichester, West Sussex, United Kingdom, under commercial practice, plants of the new *Chrysanthemum* variety 'Plum Crazy' differed from plants of the female parent 'G69D2' in the following characteristics:

1. The new variety 'Plum Crazy' produces dark purple decorative inflorescences whereas the female parent 'G69D2' produces pink decorative inflorescences.
2. In natural growth condition, plants of the new variety 'Plum Crazy' show inflorescences one week after plants of the female parent 'G69D2'.
3. The plants of the new variety 'Plum Crazy' have a more uniform growing habit than the plants of the female parent 'G69D2'.

Comparison with Male Parent

Plants of the new *Chrysanthemum* variety 'Plum Crazy' are similar to the male parent 'Cyblis' in plant habit and growth rate. However, in side-by-side comparisons in Chichester, West Sussex, United Kingdom, under commercial practice, plants of the new *Chrysanthemum* variety 'Plum Crazy' differed from plants of the male parent 'Cyblis' in the following characteristics:

1. The new variety 'Plum Crazy' produces dark purple decorative inflorescences whereas the male parent 'Cyblis' produces purple daisy inflorescences.
2. In natural growth condition, plants of the new variety 'Plum Crazy" show inflorescences one week before plants of the male parent 'Cyblis'.

Comparison with Most Similar Variety

Plants of the new *Chrysanthemum* variety 'Plum Crazy' are similar to plants of the variety 'Jenny Wren Crimson' U.S. Plant Pat. No. 16,035 in plant habit and growth rate. However, in side-by-side comparisons in Chichester, West Sussex, United Kingdom, under commercial practice, plants of the new *Chrysanthemum* variety 'Plum Crazy' differed from plants of 'Jenny Wren Crimson' in the following characteristics:

1. The new variety 'Plum Crazy' produces dark purple inflorescences and the variety 'Jenny Wren Crimson' produces crimson inflorescences.

2. Plants of the new variety 'Plum Crazy' have larger blooms than the plants of the 'Jenny Wren Crimson'.
3. In natural growth condition, plants of the new variety 'Plum Crazy' flower three weeks later than plants of 'Jenny Wren Crimson'.

BRIEF DESCRIPTION OF ILLUSTRATIONS

Typical specimens of the plant and inflorescences for the new *Chrysanthemum* variety 'Plum Crazy' are shown in the accompanying photograph. The colors shown are as true as possible within the usual limits of this kind of illustration.

FIG. 1 is a whole plant view of the new variety 'Plum Crazy' grown in a pot.

The plant shown in the illustration is around 90 days from the commencement of planting outdoors in natural season conditions.

DETAILED BOTANICAL DESCRIPTION

The following description of the new *Chrysanthemum* variety 'Plum Crazy' is of plants grown outside, natural season, in Chichester, West Sussex, United Kingdom in the month of September in 2010. The cultivar has not been observed under all possible environmental conditions. The phenotype may vary significantly with variations in the environment such as temperature, length of day and light intensity, without any variance in genotype. The commercial classification of the new variety is a garden *Chrysanthemum.*

Plants of the new variety have been grown successfully under temperature conditions averaging about 10° C. at night and about 10° C. to 25° C. during the day. The plants were grown outdoors in 4 liter pots using a loamless compost. No growth retardants were used.

To produce a commercial product, the plants need not to be pinched. The typical container size for commercial growth is 4 liters. It has been observed that the shelf life of the new variety is about 28 days with a response time of about 13 weeks natural season. The new variety is suitable for a temperature range of 10° C. to 25° C.

The new variety may be produced as a garden pot plant. The following description is with respect to a plant produced as a garden pot plant. In the description of this new *Chrysanthemum* variety, color values have been taken from The Royal Horticultural Society Colour Chart, edition 2001.

Plant

Plant type: Pot.
Habit: Domed, free branching and spreading.
Height (cm): 25.
Width (cm): 45.
Stem:
- *Length* (*cm*).—12.
- *Diameter* (*cm*).—0.5-1.
- *Texture*.—Rough.
- *Color*.—Near Grey-brown 199B.

Branching characteristics: Free branching and spreading.
Lateral branches:
- *Length* (*cm*).—6-13.
- *Diameter* (*cm*).—0.5-0.7.
- *Texture*.—Slightly rough.

Natural season flowering date: Week 38.
Vigor: Medium to tall.
Shelf life: 28 days.
Life of blooms: 28 days.
Disease (susceptibility/resistance observed): None observed to date.
Pest (susceptibility/resistance observed): None observed to date.
Drought and temperature (susceptibility/resistance observed): None observed to date.
Growth retardant type and treatment: No treatment necessary. The plants were grown for 14 weeks in natural season conditions.
Propagation:
- *Type*.—Vegetative propagation via stem cuttings.
- *Time to rooting*.—12 days with soil temperatures of 21° C.
- *Rooting habit*.—In 12 long days, a complete root system is developed.

Foliage

Number of leaves per lateral branch: 6-9.
Compound or single: Single.
Arrangement of leaves: Alternate.
- *Shape of leaf*.—Typically 5 lobed ovate.
- *Size of leaf*.—Width (cm): 1.8-3.8; Length (cm): 3-4.5.
- *Leaf apex*.—Acute.
- *Base*.—Cordate.
- *Attachment*.—Petioled.
- *Aspect*.—Slightly undulating.
- *Margin*.—Palmately lobed.
- *Surface characteristics*.—Top: Slightly pubescent. Bottom: Slightly pubescent.

Petiole:
- *Color*.—Near Yellow-green 148A.
- *Length* (*cm*).—0.8-1.
- *Diameter* (*cm*).—0.1-0.2.
- *Surface*.—Slightly pubescent.

Venation: Net, prominent mid-veins at underside.
- *Color*.—Upper side: near Yellow-green 148A. under side: near Yellow-green148A.

Color:
- *Mature leaf*.—Upper side: near Yellow-green 147A; under side: near Yellow-green 147B.
- *Young leaf*.—Upper side: near Yellow-green 147A; under side: near Yellow-green 147B.

Inflorescence

Inflorescence appearance: Matte.
Inflorescence type: Single.
Inflorescence form: Slightly cupped.
Inflorescence shape: Round.
Flowering habit: Cyme.
Number of inflorescences per branch: 6-15.
Depth of fully expanded inflorescences (cm): 1.
Diameter of fully expanded inflorescences (cm): 7.
Phyllaries:
- *Number*.—20.
- *Color*.—Near Yellow-green147A.
- *Length* (*cm*).—0.4-0.6.
- *Width* (*cm*).—0.1-0.2.
- *Texture/appearance*.—Shiny/Slightly pubescent.

Pedicel:
- *Length*.—Terminal (cm): 4-6; lateral (cm): 1-3.
- *Diameter* (*cm*).—0.2.
- *Angle from stem* (*degrees*).—45.
- *Color*.—Near Yellow-green 146B.
- *Surface*.—Slightly pubescent.

*Habit*.—Slightly curving.
*Strength*.—Medium.

Ray florets:
*Form/shape*.—Straight.
*Texture/appearance*.—Matte.
*Number per inflorescence*.—About 700.
*Length* (*cm*).—2-3; Width (cm): 1-3.
*Apex*.—Rounded.
*Base*.—Tubular.
*Margin*.—Entire.

Disc florets:
*Form/shape*.—Cylindrical.
*Texture/appearance*.—Matte.
*Number per inflorescence*.—8-15.
*Length* (*cm*).—0.3; Width (cm): 0.1.
*Diameter of disc* (*cm*).—0.3.

Fragrance: None.

Flower bud (at onset of color):
*Length* (*cm*).—0.7.
*Diameter* (*cm*).—0.9.
*Form/shape*.—Domed flat.

General inflorescence color:
1. *Ray florets, upper side*.—Immature: near Red-purple 59B. Mature: near Red-purple 61A. Older/Fading: near Red-purple 71A.
2. *Ray florets, under side*.—Immature: near Purple 77B. Mature: near Purple 77B. Older/Fading: near Purple 77C.
3. *Bud*.—Near 77B.

Inflorescence progression with age: When the inflorescence ages, the ray florets are reflexing and becoming lighter.

Reproductive Organs

Gynoecium present on ray florets:

Ray florets per individual inflorescence: Pistillate.
*Pistil number*.—Near 700.
*Stigma color*.—Near Yellow 9A.
*Stigma shape*.—Forked.
*Style color*.—Near Yellow 9B.
*Style length* (*cm*).—0.3.

Disc florets per individual flower: Pistillate.
*Pistil number*.—8-15.
*Stigma color*.—Near Yellow-orange 14A.
*Stigma shape*.—Forked.
*Style color*.—Near Yellow-green 154B.
*Style length* (*cm*).—0.4.

Androecium present on disc florets only: Staminate.
*Stamen number*.—8-15.
*Anther shape*.—Clubbed.
*Anther color*.—Near Yellow-orange 17B.
*Pollen color*.—Near Yellow-orange 14A.

Seeds: None observed.

What is claimed is:

1. A new and distinct variety of *Chrysanthemum* plant, substantially as described and illustrated herein.

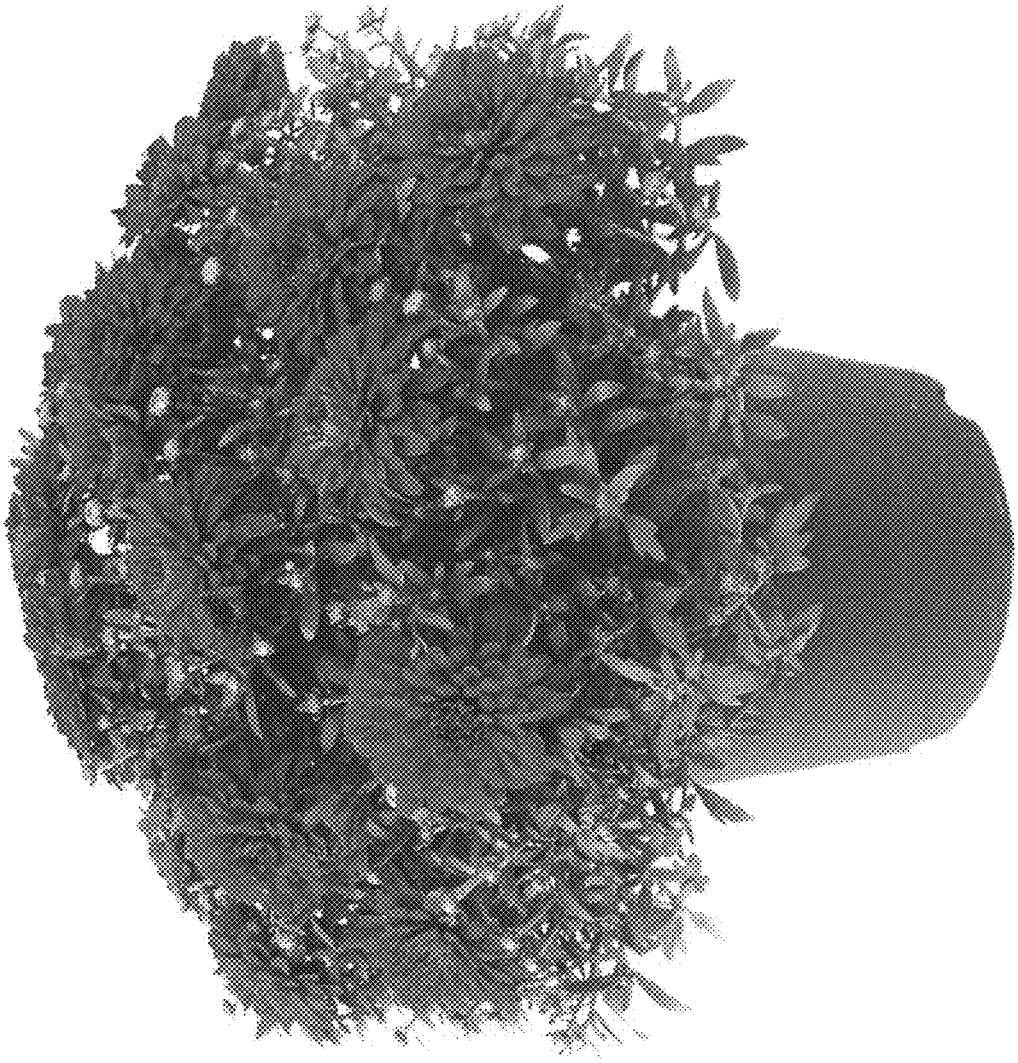

* * * * *